US007858386B2

(12) United States Patent
Medintz et al.

(10) Patent No.: US 7,858,386 B2
(45) Date of Patent: Dec. 28, 2010

(54) METHOD OF CONTROLLING QUANTUM DOT PHOTOLUMINESCENCE AND OTHER INTRINSIC PROPERTIES THROUGH BIOLOGICAL SPECIFICITY

(75) Inventors: Igor L Medintz, Alexandria, VA (US); Hedi M Mattoussi, Alexandria, VA (US); Moungi G Bawendi, Cambridge, MA (US); J Matthew Mauro, Eugene, OR (US); George P Anderson, Bowie, MD (US); Thomas Pons, Antony (FR)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 965 days.

(21) Appl. No.: 11/683,226

(22) Filed: Mar. 7, 2007

(65) Prior Publication Data
US 2008/0087843 A1 Apr. 17, 2008

Related U.S. Application Data

(60) Provisional application No. 60/779,413, filed on Mar. 7, 2006.

(51) Int. Cl.
*G01N 21/64* (2006.01)
*G01N 33/551* (2006.01)
*C12Q 1/37* (2006.01)

(52) U.S. Cl. .................. 436/172; 422/82.08; 435/6; 435/7.1; 435/23; 435/24; 435/287.2; 436/86; 436/87; 436/94; 436/501; 436/518; 436/524

(58) Field of Classification Search ... 422/82.05–82.08; 435/6, 7.1–7.2, 7.9, 287.2, 287.7, 288.7, 435/23–24; 436/86–87, 94, 172, 501, 518, 436/524
See application file for complete search history.

(56) References Cited

U.S. PATENT DOCUMENTS

| 5,981,200 | A  | * | 11/1999 | Tsien et al. | 435/7.4 |
| 6,207,392 | B1 | * | 3/2001 | Weiss et al. | 435/7.1 |
| 6,291,201 | B1 | * | 9/2001 | Garman | 435/23 |
| 6,326,144 | B1 | * | 12/2001 | Bawendi et al. | 435/6 |
| 6,410,255 | B1 | * | 6/2002 | Pollok et al. | 435/23 |
| 6,468,808 | B1 | * | 10/2002 | Nie et al. | 436/524 |
| 6,936,427 | B2 | * | 8/2005 | Kauvar | 435/7.1 |
| 6,942,987 | B2 | * | 9/2005 | Auld | 435/15 |
| 7,384,781 | B2 | * | 6/2008 | Moyle et al. | 435/287.2 |

(Continued)

OTHER PUBLICATIONS

Wang, C. et al, Applied Physics Letters 2002, 80, 4-7.*

(Continued)

*Primary Examiner*—Arlen Soderquist
(74) *Attorney, Agent, or Firm*—Amy Ressing; Roy Roberts (57) ABSTRACT

A method of controllably changing an intrinsic property of a quantum dot by using a biological entity, either attached or in close proximity to the quantum dot, and changing the state of biological entity with a controllable mechanism. The change in state of the biological entity controllably changes the intrinsic property of the quantum dot. The photoluminescence emission of quantum dots can be controlled by the present method. The methods disclosed include controlling the magnitude of QD photoluminescence as well as turning the photoluminescence on/off. The methods disclosed include using the same biological control architecture to control other intrinsic QD properties such as charge state, magnetic or other property.

15 Claims, 10 Drawing Sheets

U.S. PATENT DOCUMENTS

| | | | | |
|---|---|---|---|---|
| 7,410,793 | B2* | 8/2008 | Boege et al. | 435/288.7 |
| 7,413,868 | B2* | 8/2008 | Kauvar et al. | 435/7.2 |
| 7,645,586 | B2* | 1/2010 | Gordon et al. | 435/7.1 |
| 2001/0023078 | A1* | 9/2001 | Bawendi et al. | 436/524 |
| 2002/0019002 | A1* | 2/2002 | Griffiths | 435/6 |
| 2002/0168640 | A1* | 11/2002 | Li et al. | 435/6 |
| 2003/0027220 | A1* | 2/2003 | Colver et al. | 435/7.9 |
| 2004/0086883 | A1* | 5/2004 | Gaub et al. | 435/6 |
| 2005/0124008 | A1* | 6/2005 | Kauvar | 435/7.9 |
| 2005/0227309 | A1* | 10/2005 | Corry et al. | 435/32 |
| 2008/0153085 | A1* | 6/2008 | Patolsky et al. | 435/6 |

OTHER PUBLICATIONS

Goldman, E. R. et al, Analytical Chemistry 2002, 74, 841-847.*
Goldman, E. R. et al, Journal of the American Chemical Society 2002, 124, 6378-6382.*
Lin, C. I. et al, Biosensors and Bioelectronics 2004, 20, 127-131.*
Dwarakanath, S. et al, Biochemical and Biophysical Research Communications 2004, 325, 739-743.*
Goldman, E. R. et al, Analytica Chimica Acta 2005, 534, 63-67.*
Hahn, M. A. et al, Analytical Chemistry 2005, 77, 4861-4869.*
Chang, E. et al, Biochemical and Biophysical Research Communications 2005, 334, 1317-1321.*
Bentzen, E. I. et al, Bioconjugate Chemistry 2005, 16, 1488-1494.*
Clapp A. R. et al, Journal of the American Chemical Society 2005, 127, 18212-18221.*
van Sark, W. G. J. H. M. et al, Chemphyschem 2002, 3, 871-879.*
Fan, C. et al, Trends in Biotechnology 2005, 23, 186-192.*
Ma, Q. et al, Talanta 2005, 67, 1029-1034.*
Yaron, A. et al, Analytical Biochemistry 1979, 95, 228-235.*
Gershkovich, A. A. et al, Journal of Biochemical and Biophysical Methods 1996, 33, 135-162.*
Li, Y. et al, Bioconjugate Chemistry 1999, 10, 241-245.*
Veinot, J. G. C. et al, Polyhedron 2000, 19, 331-341.*
Trammell, S. A. et al, Bioconjugate Chemistry 2001, 12, 643-647.*
Medintz, I. L. et al, Nature Materials 2003, 2, 630-638.*
Wang, D. et al, Journal of Physical Chemistry B 2004, 108, 16642-116653.*

* cited by examiner

METHOD OF CONTROLLING QUANTUM DOT PHOTOLUMINESCENCE AND OTHER INTRINSIC PROPERTIES THROUGH BIOLOGICAL SPECIFICITY

CROSS-REFERENCE TO RELATED APPLICATIONS

This Application is a Non-Prov of Prov (35 USC 119(e)) application 60/779,413 filed on Mar. 7, 2006, incorporated herein in full by reference.

BACKGROUND OF THE INVENTION

Although biological functionalization and applications of quantum dots (QDs) have been described for previously, the focus has been on utilizing the QD photoluminescence as a fluorophore or fluorometric label or marker in a bio-assay. Earlier studies observed an increase in QD photoluminescence when proteins are specifically coordinated to the QD surface, see Mattoussi et al, Self-assembly of CdSe—ZnS quantum dot bioconjugates using an engineered recombinant protein, J Am. Soc. 122: 12142-12150 (2000); Medintz et al, Self-assembled nanoscale biosensors based on quantum dot FRET donors, *Nat. Mat.* 2: 630-638 (2003)). Medinz et al, coordinated several different proteins to the surface of QDs and monitored the effect on photoluminescence. The proteins were self-assembled or coordinated to the surface of the QDs using the HIS-Zn mechanism or metal affinity. The MBP lacking the N-terminal 5-HIS sequence was unable to coordinate to the QD and thus unable to increase QD photoluminescence. The other proteins were able to specifically coordinate to the QD surface and increase the QD photoluminescence with slightly different efficacies. Those proteins were believed to passivate QD surface charge.

Myoglobin, with a slightly smaller molecular weight, containing an internal Heme moiety (with possible electrochemical properties, as opposed to the apo-myoglobin lacking Heme) has more moderate, modulated, differing effects on the QD photoluminescence as opposed to the apo-myoglobin. This coordination of proteins increases the QDs photoluminescence in a concentration dependant manner. The coordination of proteins at or near the actual QD surface enhances the QD photoluminescence response to excitation energy by passivating the electric field effects brought by the set of charges deriving from the COOH groups arrayed around the nanoparticle surface. The surface charge of QDs (on the inorganic cores) is critical in determining whether they will be emissive or not. This has been attributed to Auger ionization process (Efros et al, Phys. Rev. Lett. 78, 1110 (1996).

Additional studies have focused on using QDs as the fluorescence resonance energy transfer (FRET) donor portion of a FRET pair consisting of QDs that are not necessarily conjugated to any other entity, coordinated to protein acceptor dyes. See Medintz et al., 2003: Clapp, et al. Fluorescence resonance energy transfer between quantum dot donors and dye labeled protein acceptors. J. Am. Chem. Soc. 126: 301-310, 2004. Although the references explore the uses of QDs in biological applications, there was no discussion of a biological strategy or mechanism that could be used for the specific control of QD properties as desired.

Additionally, although not biological in nature, the results of the Guyot-Sionnest group studies suggest that charge and charge injection can be used as a mechanism to control QD photoluminescence. Furthermore, the response of biological entities in a controlled manner has been harnessed and applied to development of sensors and other biological devices. This includes binding events, enzymatic events, hybridization events, cleavage events, as well as changes in conformation to name but a few.

The photoluminescence emission from individual CdSe QDs under continuous low intensity laser illumination is intermittent, with single dots exhibiting binary on-off emission patterns. See Nirmal, et al. Nature 383, 802 (1996), Banin, et al. J. Chem. Phys. 110, 1195 (1999) and Kuno, et al, Chem. Phys. 112, 3117 (2000). Random ionization followed by neutralization of the nanocrystals under sustained laser irradiation is the likely cause of this on-off effect. In this theory, ionized nanocrystals are dark while neutral QDs are emissive (Efros et al., 1996). According to this model, a charged quantum dot is dark as a result of an efficient Auger process. Instead of emitting a photon, an exciton in a charged dot efficiently transfers its energy to another charge in the dot, which is excited to a higher electronic state and then relaxes back to its ground state non-radiatively. Although the exact ionization and neutralization process is not yet understood, its effect is dramatic: A charged dot does not emit light. This binary turning on and off of the fluorescence by charging is a powerful property that can now be controlled in creating active nanocrystal based fluorescent nanosensors. A small QD capacitor (a thin layer of quantum dots sandwiched between two electrodes) was controllably charged by applying a voltage (Woo et al, Reversible charging of CdSe nanocrystals in a simple solid-state device, Adv. Mat. 14 (15): 1068, 2002). As the applied voltage reaches a critical point allowing charge injections QD bulk fluorescence becomes quenched by as much as 70%. Photodarkening of ensembles of CdSe—ZnS nanocrystals embedded in thin film structures, either close packed or dispersed in a matrix of ZnS, has also been observed. The darkening in these films was speculated to be the result of ionizing a substantial fraction of the dots in the films (J. Rodriguez-Viejo, et al. J. Appl. Phys. 87, 8526 (2000)).

P. Guyot-Sionnest et al. showed that by exposing a solution of colloidal CdSe QDs to strong redox molecules, an electron could be injected in the valence band of these nanocrystals. This electron (n-type) doping translated in a substantial loss (bleaching) of the first absorption peak accompanied by loss of the photoluminescence emission. These experiments were further extended to other systems and sample configurations. For example, they showed that applying a potential to a set of QDs dispersed in an electrolytic solution, results in bleaching of the first absorption peak and reduces the photoluminescence emission when the applied voltage exceeds a threshold value. Results were further extended to solid films of QDs.

Biological applications of luminescent colloidal semiconductor nanoparticles or quantum dots are only beginning to be realized. Bio-functionalization of QDs and their use as a fluorescent marker in a biological assay have been demonstrated. With the burgeoning field of nanotechnology growing every year and exploring the interface between biology and materials, many new uses and devices for QDs will be found. These new nanotechnological uses in research and other fields will require specific control of QD properties such as photoluminescence, energy absorbance and other specific QD effects/characteristics or phenomena. Currently there exists no specific and controllable manner to achieve this except for varying the amount of energy used to excite the QDs, the amount of charge used to inject electrons into the QD or through direct exposure to chemicals. Many of these methods exert gross effects on the QD for research or other purposes. Although bio-functionalization of QDs has been demonstrated, with the field growing annually, the focus has been on using the QDs as biolabeling fluorophores or energy donor in fluorescence energy transfer. None of the bio-functionalization reported has been intended for, created for or has realized control of specific QD properties.

There is a need in the art for a method for controlling the properties of luminescent colloidal quantum dots. This need is addressed by a method that is designed to be useful for controlling the properties of luminescent quantum dots through a change in state of a biological entity either in close proximity to or attached to the surface of a QD. The control of various QD properties of interest will be affected by these biological entities in a controlled manner. The control of QD properties can be affected by these biological entities in a gross or on/off absolute manner. The control of QD properties can be affected by these biological entities in a modulated or desired or controllable manner. The control of QD properties can be affected by these biological entities through the addition of an external chemical, agent or effect which in turn affects this biological entity and its subsequent control of QD properties. The control of QD properties can be affected by these biological entities in a concurrent or consecutive manner. Although control of QD properties can be affected by many different biological entities which change state in many different ways, the same basic principles and overall architecture and conceptual scheme apply. These control mechanisms may be utilized to control all aspects of QD properties of interest including, but not limited to QD absorption, emission, magnetic, charge, redox and other properties

BRIEF SUMMARY OF THE INVENTION

Disclosed is a method of controllably changing an intrinsic properly of a quantum dot by using a biological entity either attached or in close proximity to the quantum dot, and changing the state of biological entity with a controllable mechanism. The change in state of the biological entity controllably changes the intrinsic property of the quantum dot. This method can control the photoluminescence emission of luminescent colloidal semiconductor nanoparticles or quantum dots. Control of QD photoluminescence is attained through a change in state of a biological entity attached to, or in close proximity to, the QD. The biological entities can exert control through several different mechanisms including, but not limited to, the actual QD photoluminescence, on the ability of the QD to re-emit absorbed energy as photoluminescence or radioactive energy, or on the ability of the QD to absorb energy. The change in state of the biological entity includes, but is not limited to, the recognition and binding specificity provided by biological molecules, the changes in conformation of biological molecules, the enzymatic activity of biological molecules, the change in redox potential of biological molecules and chemically modified biological molecules acting as a linker and bringing the chemical functionality into close proximity of the QD which affects and changes QD photoluminescence. The methods disclosed include controlling the magnitude of QD photoluminescence as well as turning the photoluminescence on/off. The methods include using the same biological control architecture to control other intrinsic QD properties such as charge state, magnetic or other property.

Potential applications include areas where specific mechanisms for controlling the QD photoluminescence or other QD characteristics, intrinsic properties or phenomena are required. These include, but are not limited to, the following areas: nanotechnology based systems for biological and other research functioning in, but not limited to, light/energy harvesting, sensing, biosensing, medical devices, biorobotics, biological research where response to concentration of ions are important such as neurobiology, analytical chemistry including specific analyte and environmental sensing, light harvesting and energy production, as well as control and nanotechnology-based monitoring and other devices. Additionally, use of QDs in biological and other fields where the QD is an integral part of a complex macromolecular assembly and its properties are also integral to the function of that assembly in, but not limited to the areas described above.

DETAILED DESCRIPTION OF THE INVENTION

A method of controlling the spectroscopic properties of luminescent QDs (e.g. nanocrystals of CdSe) induced by charge transfer to the nanocrystal (ionization) through, for example, redox interactions with proximal redox active groups are provided. The latter can be brought in close proximity to the QD via solution phase diffusion, or in a more controllable method using conjugation to a protein/peptide that can be either externally labeled with a redox active group or engineered to express a redox center within its structure. Close proximity is defined as the distance that the biological entity is in relation to the QD. The biological entity must be close enough to exert an influence on the QD. Those skilled in the art would understand that the relative proximity is determined by the QD, the nature of the biological entity, and the type of mechanism the biological entity uses to control the QD. For example, charge-transfer has an exponential dependence on distance and so the biological entity would have to be close enough to the QD when not in contact to accomplish charge-transfer for the particular mechanism. Close proximity typically includes a separation distance ranging to about 15 nm between the biological entity and the QD.

Figure 1:
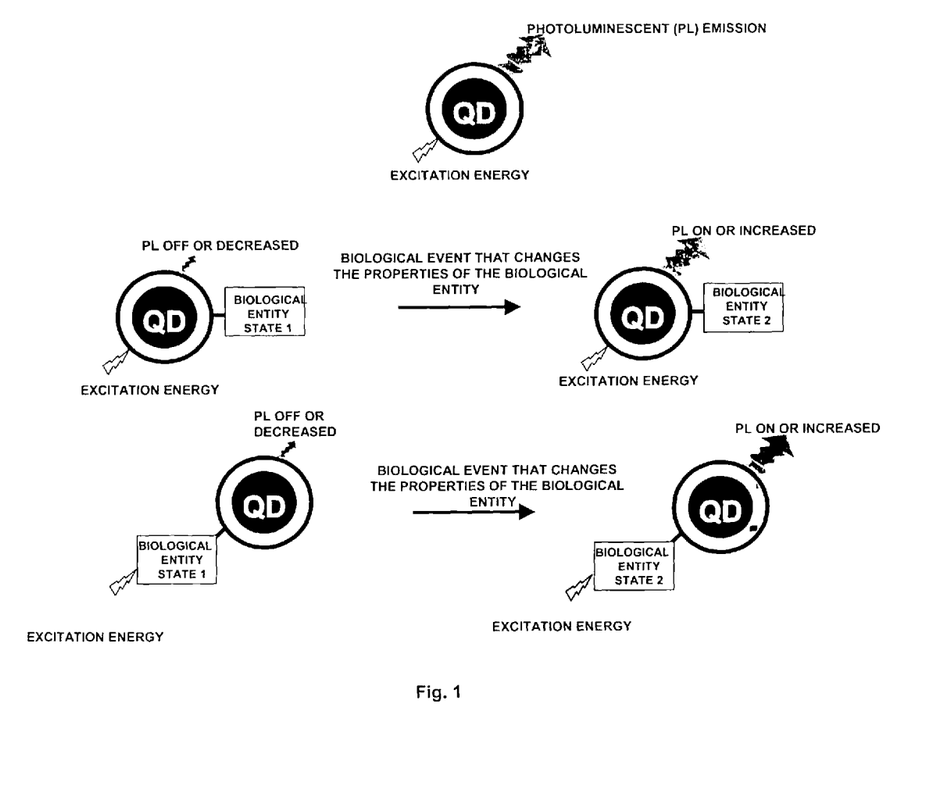
FIG. 1 shows of the mechanisms affecting QD photoluminescence emission.

FIG. 1 is a schematic of the mechanisms affecting QD photoluminescence emission. When a QD absorbs appropriate excitation energy, there is a subsequent photoluminescence emission of light at a discrete range of wavelengths. A biological entity, including but not limited to a protein or DNA, will be in near proximity or coordinated to the surface of the QD. When this biological entity is in one state the QD photoluminescence will be decreased or off, due to the mechanisms described herein. After this biological entity undergoes a biological or other modification which changes the intrinsic properties of that entity to a second state, there is a corresponding controllable and predictable effect on the QD photoluminescence emission bring it back on or increasing it. The two schemes presented demonstrate that this biological control can be exerted at several points. The biological control can affect the emission of the QD, the ability of the QD to re-emit energy, or control can also be exerted on the ability of the QD to absorb energy prior to re-emission.

The mechanism described in this document must be differentiated from the one based on Förster resonance energy transfer (FRET) which occurs between the QD and proximal dyes in either close-packed films or QD-bioconjugates. The latter involves the nonradiative transfer of excitation energy from the QD to the proximal dye and requires strong spectral overlap between donor photoemission and acceptor absorption. In contrast, there is no requirement for spectral overlap involved in the present systems. Since the present method does not rely on spectral overlap, any wavelength emitting QD can be used.

A method for controlling luminescent colloidal semiconductor nanoparticles or QD photoluminescent emission as well as other QD characteristics, intrinsic properties or phenomena as required is disclosed. The method utilizes a change in state of a biological entity, through biological or other phenomena, attached to or in near proximity to a QD to achieve control of QD photoluminescence and other properties. Possible biological entities that can be used for control, a description of the biological phenomena that would cause a change in state of the biological entities, and the possible mechanisms functioning in conjunction with the change in the biological entities that would affect control over QD photoluminescence emission are provided. The biological entities can change state and exert control through several mechanisms including, but not limited to, the recognition and binding specificity provided by biological molecule, the changes in conformation of biological molecules, the enzymatic activity of biological molecules, the change in redox potential of biological molecules or other biological molecules that affect QD surface charge or charge injection/withdrawal as well as chemically modified biological molecules acting as a linker and bringing a chemical functionality, which affects the QD into close proximity of the QD. Control methods may utilize, but are not limited to, effects exerted on the actual QD photoluminescence, on the ability of the QD to re-emit absorbed energy as photoluminescence or radiative energy or on the ability of the QD to absorb energy. Also provided for are biological methods utilizing similar architecture/design/strategy to control other intrinsic QD properties including but not limited to charge, surface charge, charge injection, magnetic, dipolar, photocatalytic or other QD characteristics, intrinsic properties or phenomena. This controlling mechanism can affect a single QD property or multiple properties concurrently or consecutively.

The entities that control QD photoluminescence or other QD properties consist of biological entities, including but not limited to, a protein, such as a receptors an antibody, and antibody fragment, or an enzyme, a modified protein conjugated to electroactive compounds/centers, photochromic compounds, photoreactive compounds, photolabile compounds. DNA, RNA, PNA, a carbohydrate, a lipid, a modified polymer, a biomimetic polymer or chemical and any derivatives thereof. The biological entity is coordinated to the surface of, or in close proximity to a QD.

The change in state of the biological entity includes, but is not limited to, be a change in protein conformation or activity caused by phosphorylation/dephosphorylation, addition of substrate, change in redox state, binding of antigen, displacement of target analog, cleavage of proteolytic site, photoactivation or heating/cooling. For DNA. RNA and PNA, the change in state includes, but is not limited to, hybridization of complement that may be derivatized with photoreactive or electroactive compounds, nuclease digestion/cleavage, and ligation/endonuclease activity to add or remove terminal modified nucleotides.

The mechanisms coupled to biological events that are used to control QD intrinsic properties include, but are not limited to, the proximity to QD of photoactive or PL absorbing species, the enzymatic cleavage of an inactive substrate to create a product that is photoactive, PL absorbing, or reactive with the QD, enzymatic cleavage of a species that is photoactive/PL absorbing or reactive with the QD to an inactive product, creation of a reactive species that disrupts QD PL, change the charge state of the QD and the PL via switching of redox state or creation of electrons, or biological entity that creates/releases/controls/energy that QD absorbs.

Examples provided herein focus on biological control of QD photoluminescence. The biological entity affects the QD photoluminescence when it is in a given state (State 1) and when this state is modulated/altered/turned off/on (State 2) there is a subsequent change in QD photoluminescence as shown in FIG. 1. The biological entity may exert control on the QD through a variety of mechanisms including, but not limited to direct absorption of QD photoluminescence through fluorescence resonance energy transfer (FRET) and other radiative or energy absorbing mechanisms, control of the QD photoluminescence emission through control of the QD surface charge state, control of other mechanisms that affect QD photoluminescence, and control of the radiative and/or other energy that the QD absorbs. A change in state of the biological entity, and thus a change in state of the QD photoluminescence, is brought about through a variety of biological phenomena including, but not limited to recognition and binding specificity and activity provided by biological molecules, changes in conformation of biological molecules, enzymatic activity of biological molecules, change in redox potential of biological molecules including any effects this redox change brings about on QD properties such as absorbance/emission or exciton donating as well as changes brought about by chemically modified biological molecules acting as linkers and bringing the chemical functionality, which affects the QD, into close proximity of the QD. Changes in QD state may be gross effects. i.e., QD on/off, or more subtle effects on QD photoluminescence magnitude, such as modulation of QD emission that may or may not be proportional to the change in state/function/activity of the biological entity.

The examples exemplify only some of the possible types of biological control over QD photoluminescence or other QD characteristics, intrinsic properties or phenomena. Using different biological components, but using the same or similar basic architecture and similar assembly methods, a large number of biological mechanisms, each having the novel features described, may be prepared to control QD photoluminescence emission or other QD characteristics in an individual or concurrent or consecutive manner as desired in a gross or magnitude-controlled manner.

The following examples demonstrate that a biological entity can be self-assembled or attached to a luminescent colloidal semiconductor nanocrystal or quantum dot and alter the QD's intrinsic photoluminescence or other properties in a controllable manner. Additionally, another biological mechanism or entity can then be used to alter the first biological entity to recover the initial QD property in a controllable manner.

A biological entity, a labeled-peptide, and/or mechanism, polyhistidine metal-affinity coordination of the labeled-peptide to the QD can be used to control and alter an intrinsic property (the photoluminescence) of a colloidal semiconductor nanocrystal. This can be accomplished in a controllable manner. The initial modulation of QD property can in turn be controlled and altered by a second biological process, the enzymatic proteolysis of the labeled peptide. These examples were performed in the format of an actual biological assay.

Figure 2:
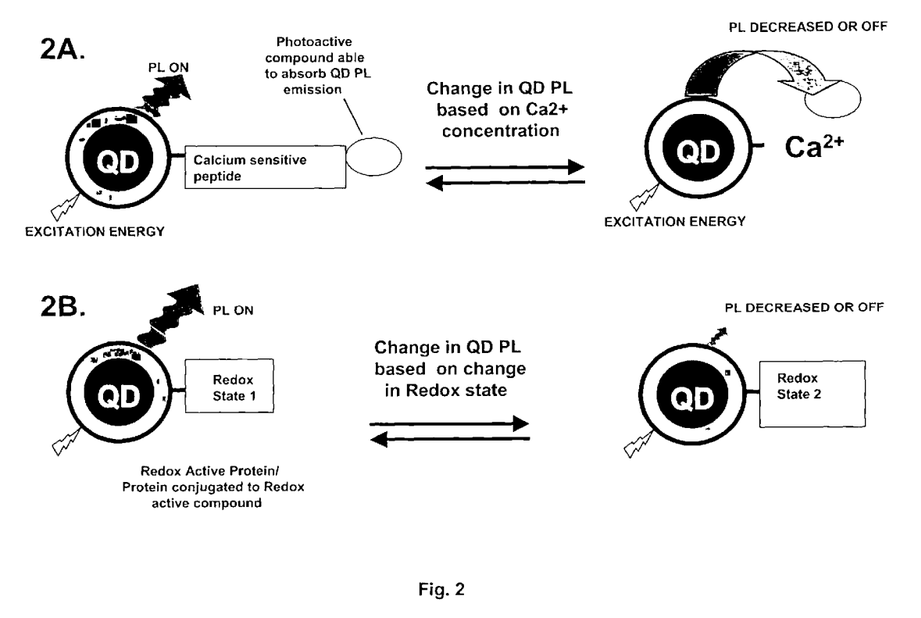
FIG. 2 is a schematic showing the mechanism for reversible control of QD photoluminescence by a photoactive compound.

FIG. 2 is a schematic showing the mechanism for reversible control of QD photoluminescence by a photoactive compound. FIG. 2A shows a redox active compound, in FIG. 2B, both conjugated to a protein which is conjugated to the surface of a QD. In FIG. 2A, the reversible response and change in conformation of a calcium binding peptide brings a photoactive compound into and out of critical proximity to the QD, which controls the QDs photoluminescence in a concentration dependent manner. FIG. 2B shows a control mechanism, where a QD is conjugated to a redox active protein whose state can be changed by some biological or other event. The change in redox state affects the surface charge state of the QD and thus its photoluminescence emission. Although only one biological control mechanism is shown per QD, several can be coordinated to each QD in a controllable radiometric method.

Figure 3:
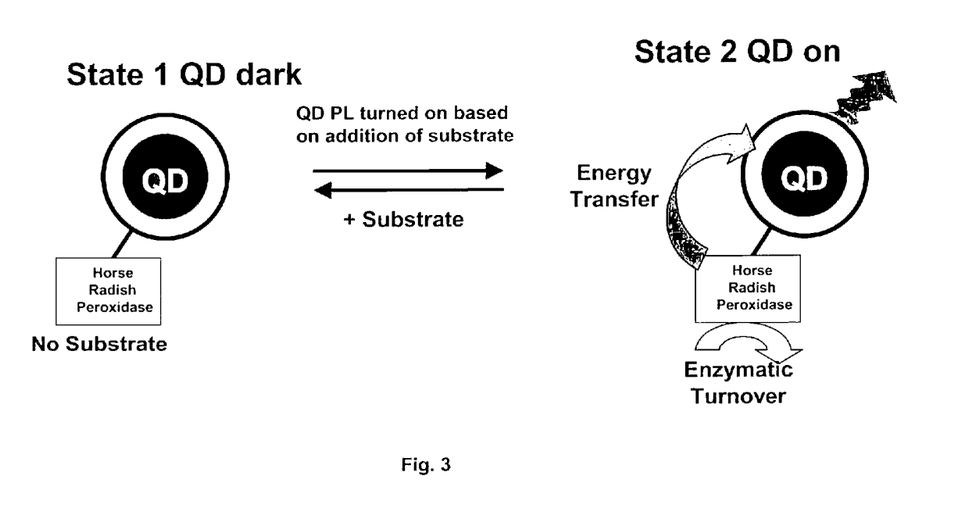
FIG. 3 is a schematic of the mechanism for reversible control of QD photoluminescence by a protein with enzymatic function that is coordinated to the surface of the QD.

FIG. 3 shows a schematic of the mechanism for reversible control of QD photoluminescence by a protein with enzymatic function that is coordinated to the surface of the QD. In this scenario, the enzyme is horse radish peroxidase, which catalyzes the conversion of luminol in the presence of $H_2O_2$ with the subsequent release of light. Since the enzyme controls the production and quantity of light the QD is exposed to, it is able to control QD photoluminescence. The control mechanism functions on the amount of energy/light the QD is able to absorb in this case. This is directly proportional to the amount of light generated which in turn is predicated or proportional to the amount of substrate present or added to the mixture.

Figure 4:
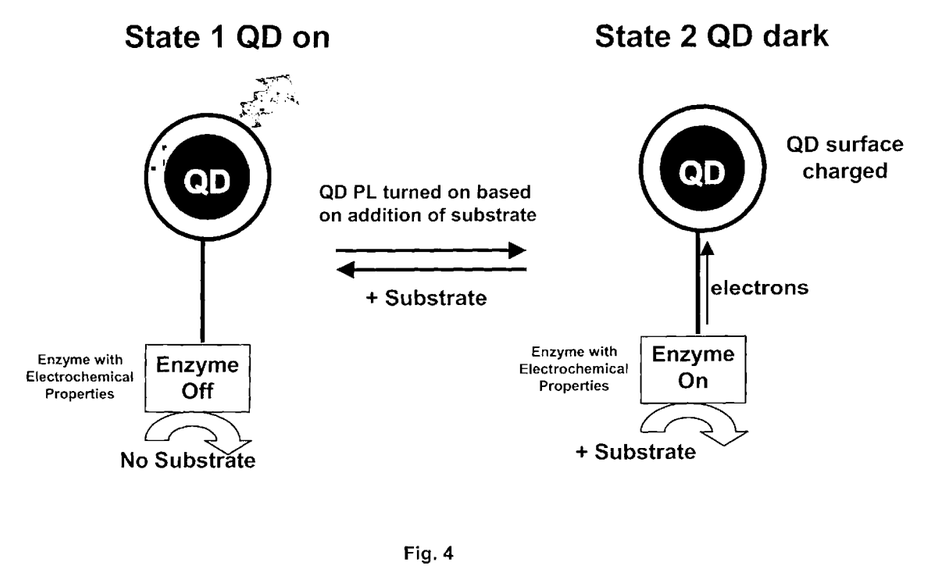
FIG. 4 is a schematic of the mechanism for reversible control of QD photoluminescence by a protein attached to the surface of the QD with enzymatic/electrochemical function that results in production of electrons.

FIG. 4 shows a schematic of the mechanism for reversible control of QD photoluminescence by a protein attached to the surface of the QD with enzymatic/electrochemical function that results in production of electrons. In this case the production of electrons results in the QD surface becoming charged and thus the QD is dark. Again the control mechanism is proportional to the amount of substrate added.

Figure 5:
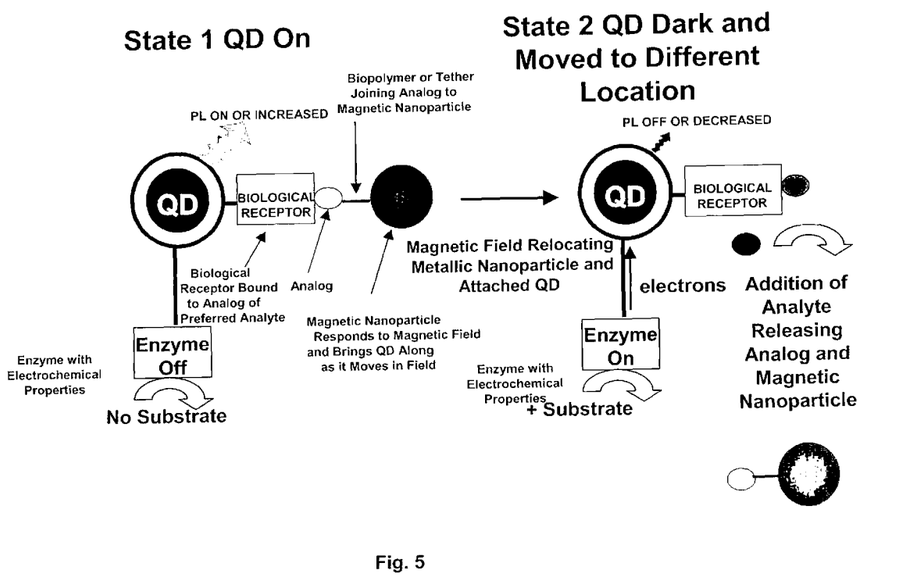
FIG. 5 is a schematic of the mechanism for controlling the QD photoluminescence and location by proteins coordinated to the surface of the QD.

FIG. 5 shows a schematic of the mechanism for controlling the QD photoluminescence and location by proteins coordinated to the surface of the QD. One of the proteins has enzymatic/electrochemical function and this results in production of electrons and quenching of QD photoluminescence as in FIG. 4. The second protein is a receptor which is able to bind an analog of its desired analyte. This analog is in turn tethered to a metallic nanoparticle. This scheme allows the protein conjugated to QD to be moved to a new location via a magnetic field. The response to this magnetic field and movement can be stopped through addition of preferred analyte. The QD photoluminescence can also be shut off by enzymatic production of electrons from the first protein when desired. FIG. 5 shows that QD properties, including location, can be controlled as desired in a consecutive or concurrent manner.

Figure 6:
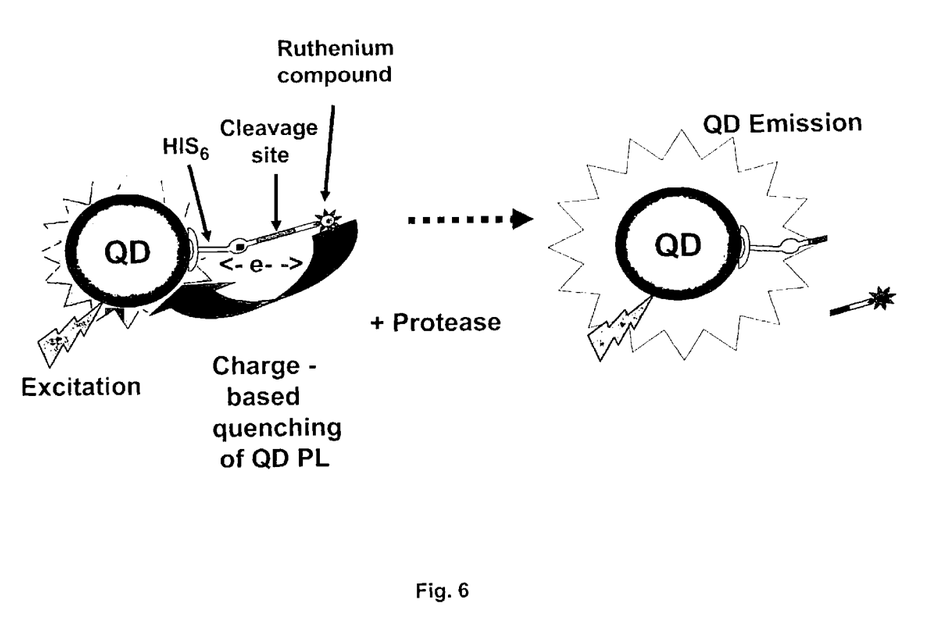
FIG. 6 is a an example where ruthenium labeled peptides were allowed to self assemble onto the surface of QDs by polyhistidine-$HIS_6$ metal affinity coordination to the Zn surface of CdSe/ZnS core shell QD capped with dihydrolipoic acid.

FIG. 6 shows an example where ruthenium labeled peptides were allowed to self assemble onto the surface of QDs by polyhistidine-$HIS_6$ metal affinity coordination to the Zn surface of CdSe/ZnS core shell QD capped with dihydrolipoic acid. The increasing ratio of the Ru-peptide on the surface of the QD causes a charge based quenching of the QD photoluminescence. Control over the ratio of peptide added per QD controls the amount of QD quenching. The peptide contains a cleavage site specifically recognized by a protease Chymotrypsin in this case. Addition of Chymotrypsin cleaves the peptide in a concentration dependent manner and allows recovery of QD photoluminescence in a concentration dependent manner.

Figure 7A:
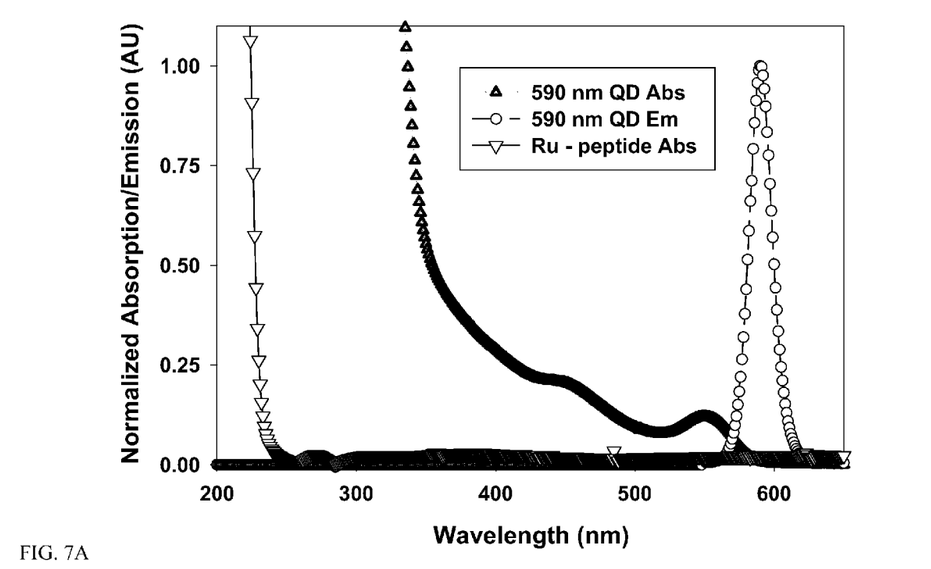
FIG. 7 shows the absorption and emission spectra of the example.

The photoluminescence properties of CdSe—ZnS (and CdSe) QDs were altered following interaction with proximal electroactive ruthenium (Ru) maleimide. Peptides with sequences designed to be substrates for specific proteases and terminated with a polyhistidine 9($His_6$) tract were labeled with the ruthenium (Ru) maleimide complex, then conjugated to luminescent QDs. The $His_6$ tract allows metal-affinity driven self-assembly on hydrophilic CdSe—ZnS QDs capped with the solubilizing agent dihydrolipoic acid (DHLA). Conjugation of the Ru-labeled peptides to the QDs reduced the QD intrinsic photoluminescence properties in a systematic and controllable manner. When appropriate protease is added to the solution containing the QD-peptide-Ru assemblies, it cleaves the peptide substrate and displaces the redox group away from the QD, resulting in a concentration-dependent recovery of the QD signal (FIG. 7A). This demonstration constitutes a specific proteolytic assay employing redox interactions for transduction mechanism. Alteration of the QD photoluminescence during assembly and following proteolytic cleavage thereafter is attributed to charge transfer (redox interactions) between the QD surface and the Ru complex.

A 17-residue peptide having the peptide sequence, N-($His_6$)-Gly-Leu-Aib-Ala-Ala-Gly-Gly-His-Tyr-Gly-Cys*-COOH, wherein ($His_6$) is the QD attachment or self-assembly domain. Tyr is recognized and cleaved by Chymotrypsin, and Cys* is the labeling site, was labeled with an electroactive ruthenium (Ru) malemide compound having the following formula:

see (Trammell, et al, Synthesis and Characterization of a Ruthenium(II)-Based Redox Conjugate for Reagentless Biosensing Bioconjugate Chem. 2001, 12, 643-647). This compound is known to mediate electron transfer and was originally designed for reagentless biosensing. The polyhistidine sequence ($His_6$) allows the peptide to self-assemble onto the QDs via metal-affinity coordination. The Tyr residue is recognized by Chymotrypsin which cleaves the adjacent bond. The Cys* residue contains a thiol for modification with the maleimide-activated Ru compound. This compound does not have spectral overlap with the QDs used in these experiments, as shown in FIG. 7A, which precludes fluorescence resonance energy transfer mechanisms.

Figure 7B:
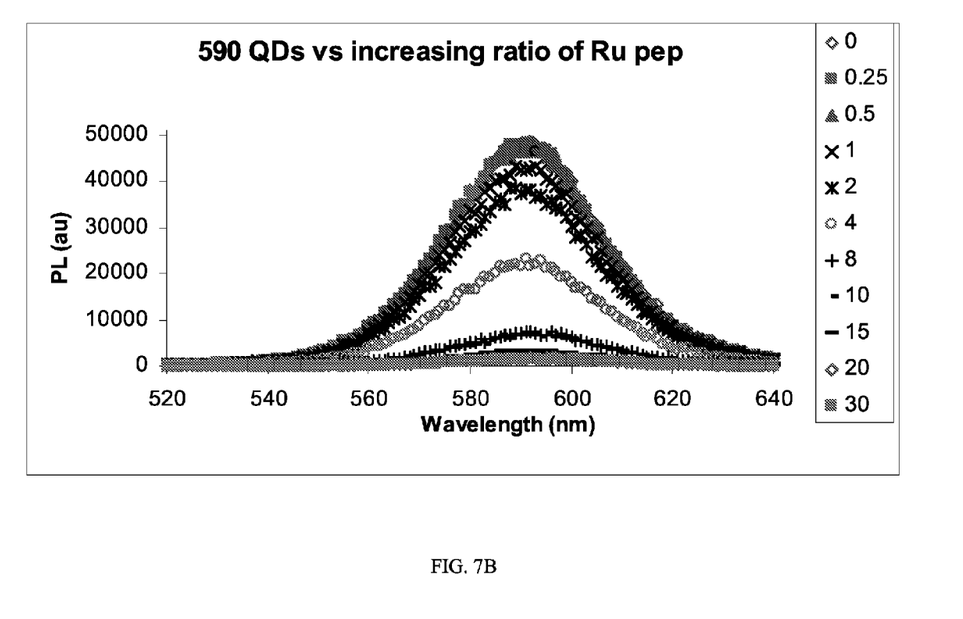
Figure 7C:
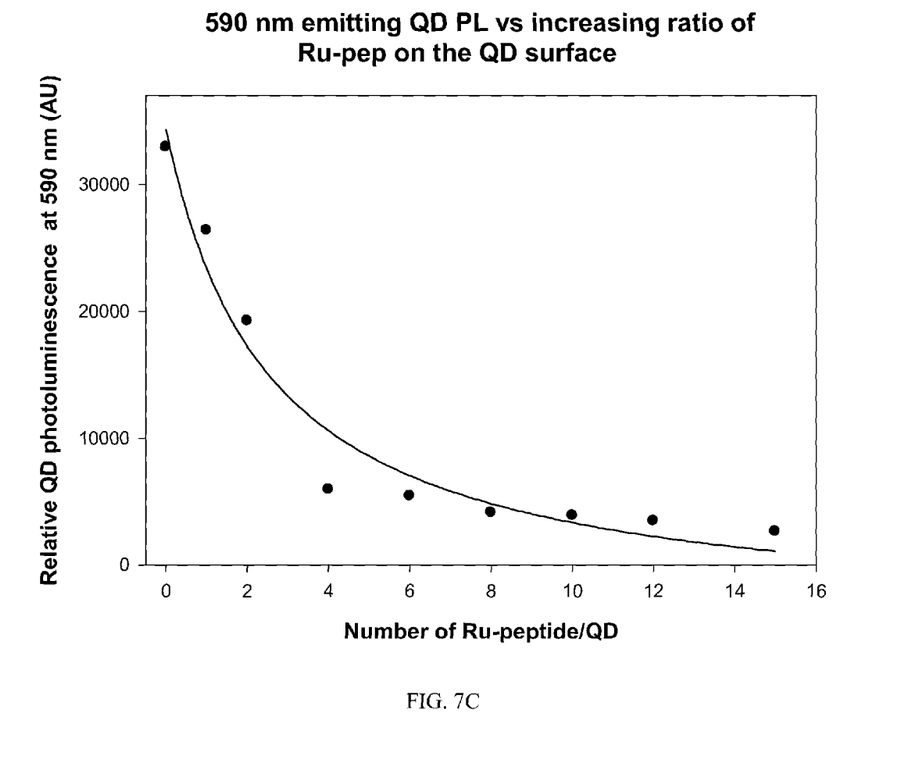
Figure 8:
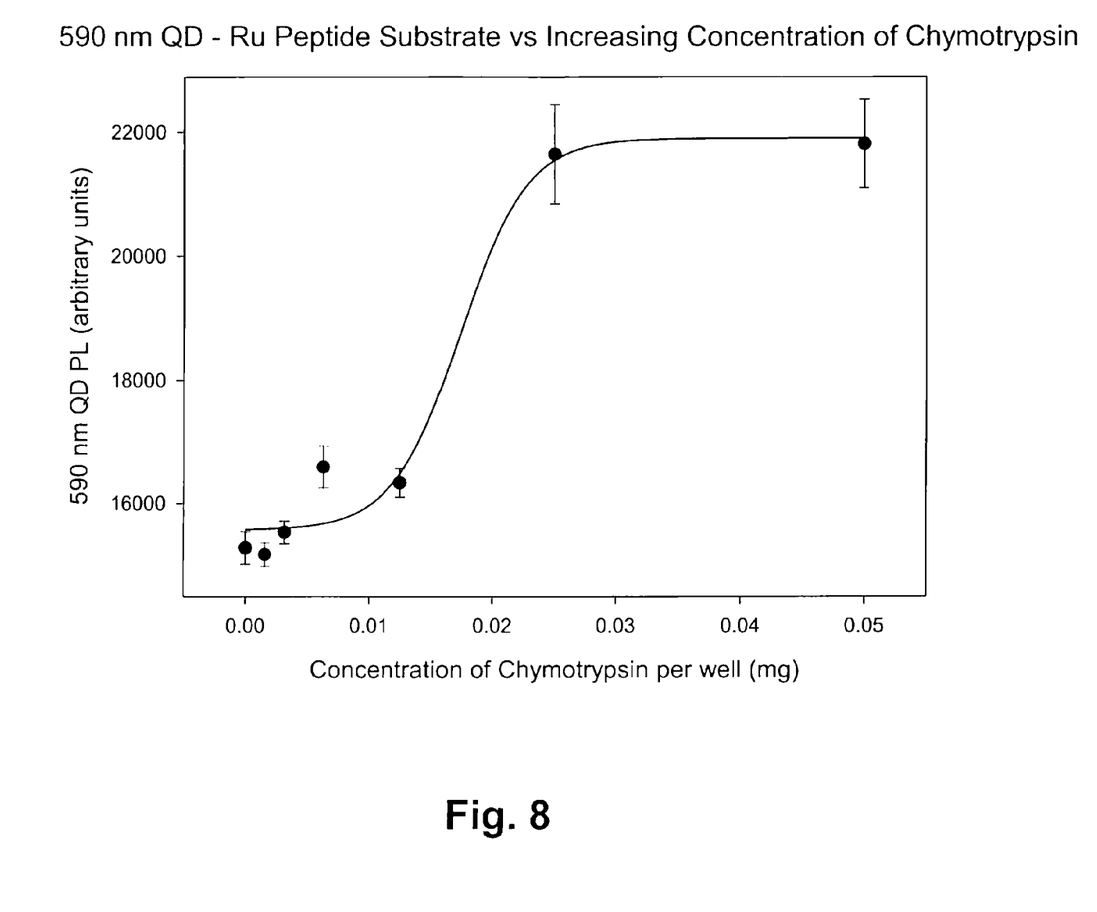
FIG. 8 is a shows the results from exposing a solution of 590 nm QDs bioconjugated with the equivalent of 4-Ru labeled peptides/QD to an increasing concentration of the protease Chymostrypsin.

When the Ru-labeled peptide is self-assembled onto the QD surface, it causes a concentration dependent decrease in the QD photoluminescence, as shown in FIGS. 7B and 7C. The reduction in QD photoluminescence is attributed to charge-mediated processes taking place on the QD surface and within the QD. The labeled peptide facilitates these processes. The addition of an enzyme (Chymotrypsin) which specifically recognizes and cleaves this peptide results in a concentration dependent increase in QD photoluminescence, as shown in FIG. 8. A first biological entity and mechanism, the metal-affinity driven coordination and self-assembly of a Ru-labeled peptide onto QDs, served to control and quench the QDs photoluminescence in a controllable manner. A second biological entity and mechanism, the specific enzymatic cleavage by a protease of the QD-surface located Ru-labeled peptide, functioned to alter and recover the QD photoluminescence in a controllable manner, concentration dependence in this case. The QD-Ru-labeled peptide bioconjugate acts as a sensor for the biological activity of the enzymatic protease—Chymotrypsin. By altering the recognition sequence expressed on the peptide to that recognized by another protease, the QD-Ru-labeled peptide bioconjugate configuration can be used as a sensor for that second protease.

FIG. 7(A) shows the absorption and emission spectra of 590 nm emitting QDs superimposed over the absorption spectra of the Ru labeled peptide. Note that the peptide does not have any appreciable absorption where the QD emits. FIG. 7(B) shows the composite spectra for increasing ratio of Ru-labeled peptide to self-assemble onto the surface of 590 nm emitting QDs. The coding of the number of peptide/QD is indicated on the right. Note the concentration dependence and that addition of ~30 Ru-peptide/QD results in >95% quenching of QD photoluminescence. FIG. 7(C) is the graphical plot of the 590 nm QD photoluminescence in (B) vs. the number of Ru-peptides assembled/QD.

FIG. 8 shows the results from exposing a solution of 590 nm QDs bioconjugated with the equivalent of 4-Ru labeled peptides/QD to an increasing concentration of the protease Chymotrypsin which recognizes and cleaves the peptide, thus increasing the QD photoluminescence.

A complementary proof of this concept is provided by measurements of changes in the absorption properties of the QDs after conjugation to Ru-labeled peptides. FIG. 7 shows the photoluminescence spectra of DHLA-capped QDs alone and QD-peptide-Ru conjugates, together with the corresponding differential absorption spectra. The loss of the QD emission is coupled with bleaching of the QD first absorption peak. Bleaching (total or partial) of the first absorption peak is due to occupation of the 1S electronic level by the injected charge, which no longer contributes to the absorption spectrum.

Biosensing based on quantum dot redox interactions has potential applications in clinical and diagnostic assays and in drug discovery. It also has advantages over current designs in that it does not rely on spectral overlap (as required in FRET), the same redox group can be compatible with a wide range of QDs (different sizes, different materials), the rate of QD quenching desired in a particular assay can be controlled by adjusting the ratio of redox groups made to interact with each QD, and it potentially allows for simultaneous monitoring or "multiplexing."

Those skilled in the art would understand that the present methods are applicable to control QD PL and other intrinsic QD properties both temporally and spatially. Such control can be exerted both concurrently or consecutively. Such control can be exerted in gross or more finely controlled manner. The method can simplify an assay scheme for biosensing by allowing monitoring of the QD emission portion alone. Additionally, the rate of QD quenching desired in a particular assay can be controlled by adjusting the ratio of the labeled charged moiety attached to each QD. Additionally the present method allows for simultaneous monitoring or 'multiplexing' in the same assay format.

Obviously, many modifications and variations of the present invention are possible in light of the above teachings. It is therefore to be understood that, within the scope of the appended claims, the invention may be practiced otherwise than as specifically described.

The invention claimed is:

1. A method of controllably and reversibly changing an intrinsic property of a quantum dot comprising:
   providing a quantum dot having an intrinsic property;
   providing a first biological entity in close proximity to said quantum dot which changes the intrinsic property of the quantum dot, said biological entity having a state; and
   changing said state of said biological entity with a controllable mechanism, wherein said change in said state controllably reverses said change in said intrinsic property of said quantum dot, said controllable mechanism comprising providing a second biological entity in close proximity to said first biological entity at a selected concentration, wherein said second biological entity alters said state of said first biological entity, thereby reversing said change in the intrinsic property of the quantum dot by a controlled amount dependent on said concentration,
   wherein the method does not rely on spectral overlap.

2. The method of claim 1 wherein said intrinsic property of said quantum dot is photoluminescence, charge state, surface charge, charge injection, magnetic, dipolar, or photocatalytic.

3. The method of claim 1 wherein said biological entity is a protein, DNA, a carbohydrate, a lipid, a bio-functional polymer or other chemical entity, a bio-mimic or any derivatives thereof.

4. The method of claim 1 wherein said controllable mechanism is the recognition and binding specificity provided by biological molecules, the changes in conformation of biological molecules, the enzymatic activity of biological molecules, the change in redox potential of biological molecules, or chemically modified biological molecules acting as a linker and bringing the chemical functionality into close proximity of the QD.

5. The method of claim 1 wherein said changing of state of said biological entity controls the QD photoluminescence emission through control of the QD surface charge state, control of other mechanisms that affect QD photoluminescence, or control of the radiative or other energy that the QD absorbs.

6. The method of claim 1 wherein said first biological entity is attached to said quantum dot.

7. A method of controlling energy absorption in a quantum dot comprising:
   providing a quantum dot;
   providing a first biological entity in close proximity to said quantum dot said biological entity having a state which changes the intrinsic property of the quantum dot; and
   changing said state of said biological entity with a controllable mechanism, wherein said change in said state controls the quantum dot energy absorption, said controllable mechanism comprising providing a second biological entity in close proximity to said first biological entity at a selected concentration, wherein said second biological entity alters said state of said first biological entity, thereby reversing said change in the intrinsic property of the quantum dot by a controlled amount dependent on said selected concentration, wherein the method does not rely on spectral overlap.

8. The method of claim 7 wherein said first biological entity is a protein, DNA, a carbohydrate, a lipid, a bio-functional polymer or other chemical entity, a bio-mimic or any derivatives thereof.

9. The method of claim 7 wherein said controllable mechanism is the recognition and binding specificity provided by biological molecules, the changes in conformation of biological molecules, the enzymatic activity of biological molecules, the change in redox potential of biological molecules, or chemically modified biological molecules acting as a linker and bringing the chemical functionality into close proximity of the QD.

10. The method of claim 7 wherein said changing of state of said biological entity controls the QD photoluminescence emission through control of the QD surface charge state, control of other mechanisms that affect QD photoluminescence, or control of the radiative or other energy that the QD absorbs.

11. A method of controllably changing the photoluminescence properties of a quantum dot comprising:
providing a quantum dot having a photoluminescence property;
providing a labeled peptide in close proximity to said quantum dot wherein said labeled peptide causes a change in said photoluminescence of said quantum dot; and
cleaving said label from said labeled peptide with a selected amount of an enzyme to controllably reverse said change to said photoluminescence of the quantum dot by an amount dependent on the amount of the enzyme,
wherein the peptide label comprises ruthenium.

12. The method of claim 11 wherein said labeled peptide is attached to said quantum dot.

13. The method of claim 12 wherein said labeled peptide is attached to said quantum dot by a $(His)_6$.

14. The method of claim 11 wherein said peptide contains a Tyr and Cys* is the labeling site on said peptide.

15. The method of claim 14 wherein the enzyme is Chymotrypsin.

* * * * *